United States Patent
Nevyas-Wallace et al.

(10) Patent No.: US 8,992,560 B2
(45) Date of Patent: Mar. 31, 2015

(54) EXPANDABLE SHIELD INSTRUMENT FOR USE IN INTRAOCULAR SURGERY

(71) Applicants: Anita Nevyas-Wallace, Narberth, PA (US); Benjamin Wallace, Narberth, PA (US)

(72) Inventors: Anita Nevyas-Wallace, Narberth, PA (US); Benjamin Wallace, Narberth, PA (US)

( * ) Notice: Subject to any disclaimer, the term of this patent is extended or adjusted under 35 U.S.C. 154(b) by 34 days.

(21) Appl. No.: 13/773,754

(22) Filed: Feb. 22, 2013

(65) Prior Publication Data

US 2013/0172900 A1 Jul. 4, 2013

Related U.S. Application Data

(63) Continuation of application No. 12/681,654, filed as application No. PCT/US2008/078753 on Oct. 3, 2008, now Pat. No. 8,449,568.

(60) Provisional application No. 60/977,867, filed on Oct. 5, 2007.

(51) Int. Cl.
| | |
|---|---|
| *A61M 29/00* | (2006.01) |
| *A61B 19/00* | (2006.01) |
| *A61F 9/007* | (2006.01) |
| *A61B 17/34* | (2006.01) |

(52) U.S. Cl.
CPC ............... *A61B 19/24* (2013.01); *A61F 9/007* (2013.01); *A61B 17/3423* (2013.01); *A61B 2019/4036* (2013.01); *A61B 2019/481* (2013.01)
USPC .......................................... 606/191; 600/219

(58) Field of Classification Search
USPC ................. 606/107, 151, 166, 191, 193–199; 623/6.12; 600/201
See application file for complete search history.

(56) References Cited

U.S. PATENT DOCUMENTS

| | | | |
|---|---|---|---|
| 2,202,748 A | 4/1938 | Solo | |
| 4,257,406 A * | 3/1981 | Schenk | 600/219 |
| 4,643,185 A | 2/1987 | Gaba | |
| 4,750,498 A | 6/1988 | Graham | |
| 5,195,505 A | 3/1993 | Josefsen | |
| 5,403,323 A | 4/1995 | Smith | |
| 7,226,451 B2 | 6/2007 | Shluzas et al. | |
| 2005/0245942 A1 * | 11/2005 | DiPoto | 606/108 |

FOREIGN PATENT DOCUMENTS

WO WO 96/06583 3/1996

OTHER PUBLICATIONS

International Search Report, dated Mar. 23, 2009, issued in priority International Application No. PCT/US2008/078753.

* cited by examiner

*Primary Examiner* — Ryan Severson
*Assistant Examiner* — Rachel S Papeika
(74) *Attorney, Agent, or Firm* — Saul Ewing LLP

(57) ABSTRACT

An instrument capable of providing large-area shielding within an isolated operating region, such as the eye, while being passable through a small incision in the region through which the instrument must be inserted. For example, an instrument capable of being passed through a typical 3 mm (or smaller) phacoemulsification incision without undue damage to ocular tissue, and which expands to provide large-area shielding, e.g. to occlude a large-diameter (e.g. approx. 6 mm) posterior capsule opening. The surgical instrument includes two or more leaves, the leaves being interconnected by at least one fastener in a manner that causes expansion of a leading or distal portion of the instrument when the following or proximal portions of each leaf are manipulated, whether by a user or through interaction with a wall of the incision.

16 Claims, 15 Drawing Sheets

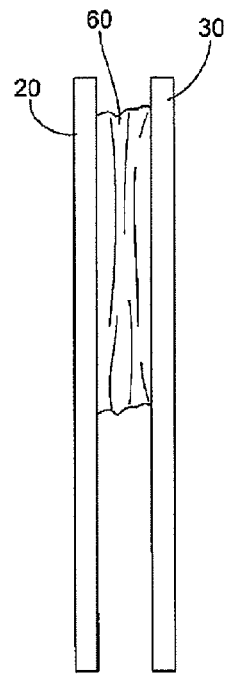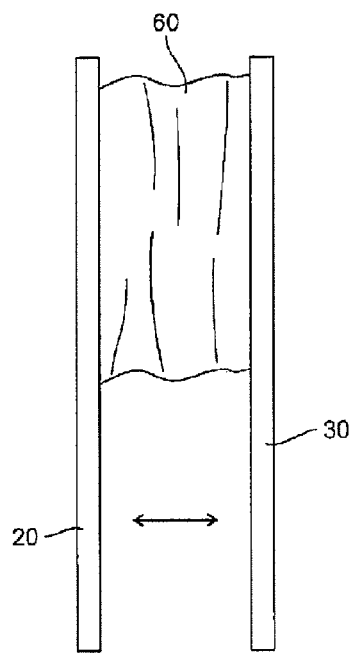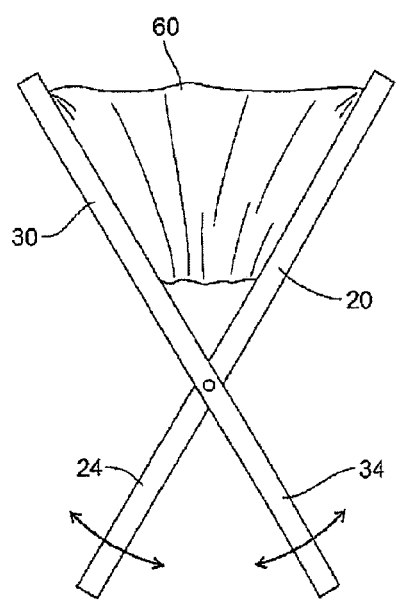
Fig. 11  Fig. 12  Fig. 15
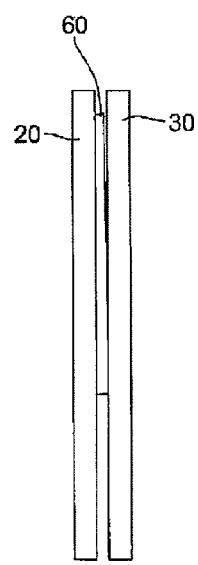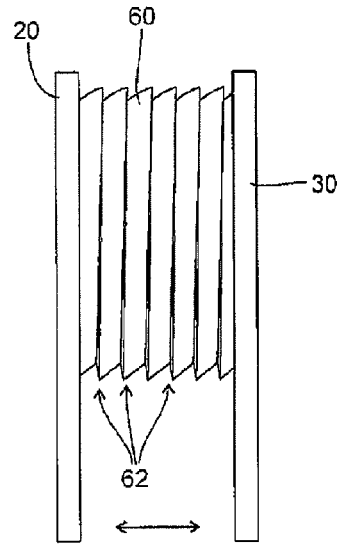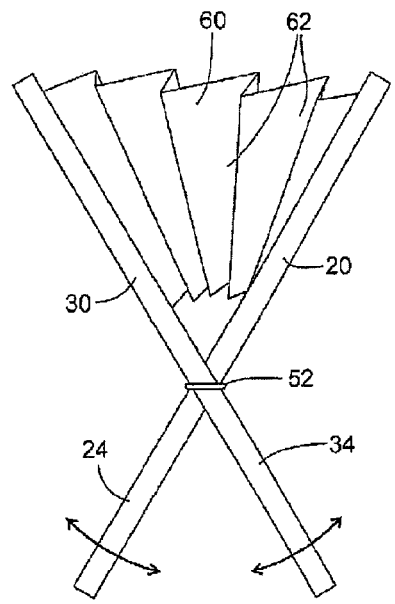
Fig. 13  Fig. 14  Fig. 16

EXPANDABLE SHIELD INSTRUMENT FOR USE IN INTRAOCULAR SURGERY

CROSS REFERENCE TO RELATED APPLICATIONS

This application is a continuation of U.S. application Ser. No. 12/681,654, filed on May 17, 2010, which claims the priority of PCT/US2008/078753, filed on Oct. 3, 2008, which is based on and claims priority to U.S. Provisional Application No. 60/977,867, filed Oct. 5, 2007, the entire contents of which are hereby incorporated fully herein by reference.

FIELD OF THE INVENTION

The present invention relates generally to instruments for use in intraocular surgery, and more particularly to an instrument capable of providing large-area shielding within the eye, yet being passable through a small incision into the eye.

DISCUSSION OF RELATED ART

Various surgical procedures involve placement of instruments through an incision made in ocular tissue. Exemplary surgical procedures include a phacoemulsification procedure in which a small incision is made in the cornea by a keratome or similar flat-bladed knife. The incision is necessary to permit insertion of instruments into the eye, and to provide access to inner portions of the eye during the surgical procedure. Because the incision damages ocular tissue, it is desirable that the damage be limited, and thus that the incision not exceed about 3 mm in length. In this exemplary procedure, a phacoemulsification probe is then inserted through the incision and is operated to create high-frequency sound waves that break up and/or emulsify the nucleus of the eye's lens, which is relatively hard tissue, then aspirate that emulsified tissue through the small incision. An irrigation/aspiration instrument may then be inserted through the incision to aspirate the cortex of the lens via suction. A foldable intraocular lens (IOL) may then be inserted through the incision, using an appropriate cartridge and injector, and into the capsular bag of the eye.

The wall of the lens capsule is extremely delicate, and posterior capsular rupture is not uncommon. Such rupture carries with it the risk of posterior segment complications and continuing inflammation if cortical and nuclear material released during phacoemulsification of the lens descends to the posterior compartment. Retention of lens material posteriorly also may necessitate subsequent posterior compartment surgery, with its attendant inconvenience and risk.

A number of instruments and techniques have been devised to minimize loss of lens material into the posterior compartment during cataract surgery that has been complicated by a tear of the posterior capsule. These include placement of a lens glide through the phacoemulsification incision, placement of viscoelastic material, either through the original incision or through a pars plana (posterior) incision, and placement of instruments, some of which have expanding basket-like protuberances, through a pars plana incision.

Insertion of a widely-used Sheets lens glide behind the lens material early after posterior capsular rupture has been detected is a rapid and simple method for attempting to limit loss of lens material into the posterior compartment. Such a Sheets lens glide is a disposable, thin (e.g., 6 mil), small (e.g., 2.8 mm by 30 mm) sterile sheet of polyethylene, such as that manufactured and/or sold by Texas Technology of Austin, Tex., USA under the trademark Cleanfilm, or other plastic material that is generally rectangular in shape, and has a width of no more than the 3 mm (or smaller) incision, to permit it to be inserted through the 3 mm (or smaller) incision made in the ocular tissue. Accordingly, the portion of the lens guide positioned intraocularly cannot effectively prevent lens material from descending to the posterior compartment; phacoemulsified lens material may easily pass beside and behind the 3 mm (or smaller) wide lens guide. Viscoelastic material does not present a solid barrier to posterior migration of lens material, and any technique requiring creating and placing instruments through a pars plana incision entails additional risk of vitreous disruption, retinal tear, choroidal hemorrhage, and vitreous hemorrhage. Furthermore, such techniques do not provide a barrier to prevent substantial loss of lens material backward into the posterior compartment, especially if the pupil is larger than 3 mm in diameter.

SUMMARY

The present invention provides an instrument capable of providing large-area shielding within the eye, while being passable through a small incision through which the instrument must be inserted into the eye. More specifically, the present invention provides an instrument capable of being passed through a typical 3 mm (or smaller) phacoemulsification incision without undue damage to ocular tissue, and which expands to provide large-area shielding, e.g. to occlude a large-diameter (e.g. approx. 6 mm) posterior capsule opening.

In one embodiment, the instrument is specially configured to expand automatically, through the action of insertion through the incision, and to collapse automatically, through the action of withdrawal through the incision. In one embodiment, the surgical instrument includes two or more leaves, the leaves being interconnected by at least one fastener in a manner that causes expansion of a (leading/distal) portion of the instrument when the (following/proximal) portions of each leaf are manipulated by a user.

BRIEF DESCRIPTION OF THE DRAWINGS

FIGS. 11 and 12 are plan views of another alternative embodiment of the instrument;

FIGS. 13 and 14 are plan views of yet another alternative embodiment of the instrument;

FIG. 15 is a plan view of an alternative embodiment of the instrument of FIGS. 11 and 12; and FIG. 16 is a plan view of an alternative embodiment of the instrument of FIGS. 13 and 14.

DETAILED DESCRIPTION

The present invention provides an instrument capable of providing large-area shielding within the eye, e.g. a shielding surface having an approximate maximum length and maximum width each greater than 3 mm, and/or providing a shielding area greater than approximately 9 mm$^2$ and preferably greater than approximately 5 mm in diameter and/or greater than approximately 19 mm$^2$. The instrument is specially-configured to provide such large-area shielding and yet to be passable through a small slit-like incision, e.g. 3 mm or less in width, through which the instrument must be inserted into the eye during ocular surgery.

Figure 1:
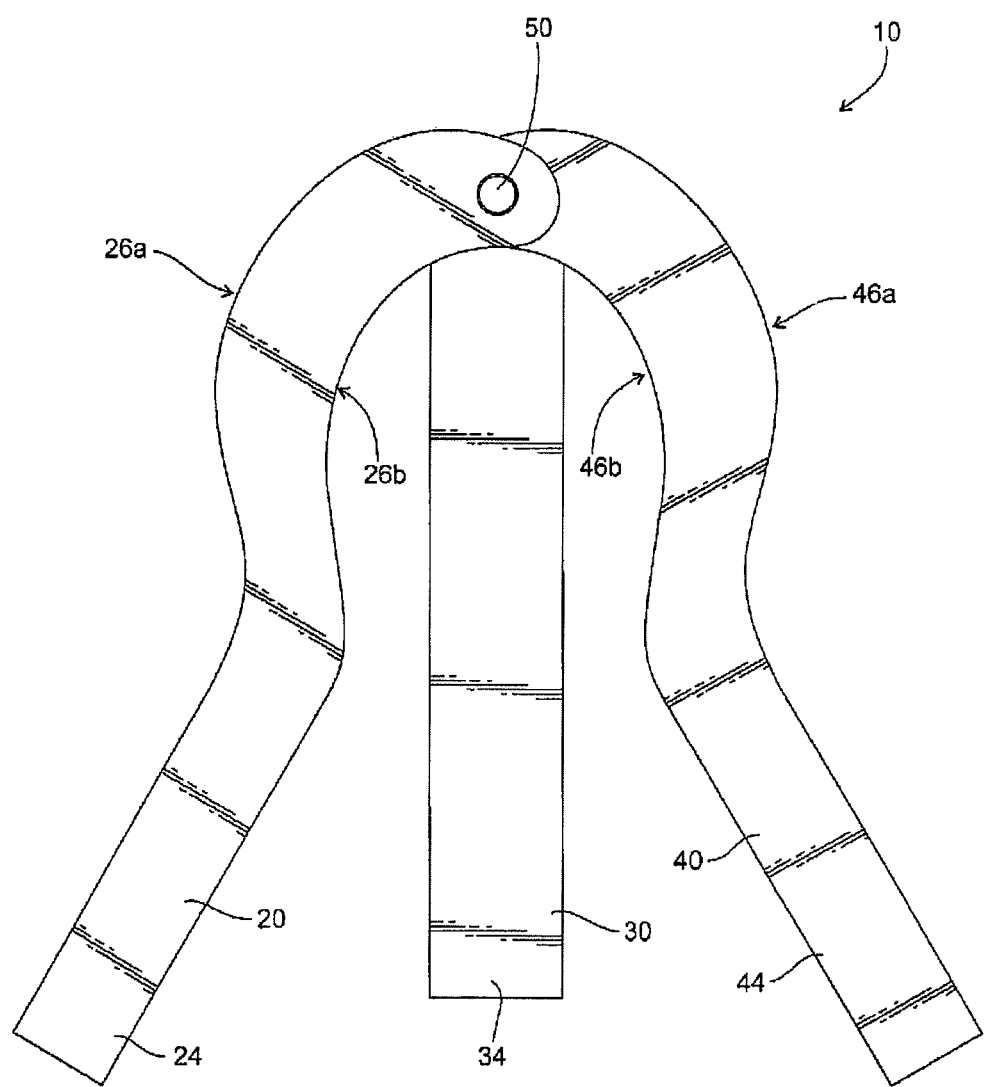
FIG. 1 is a plan view of an expandable shield instrument in accordance with an exemplary embodiment of the present invention.
Figure 2:
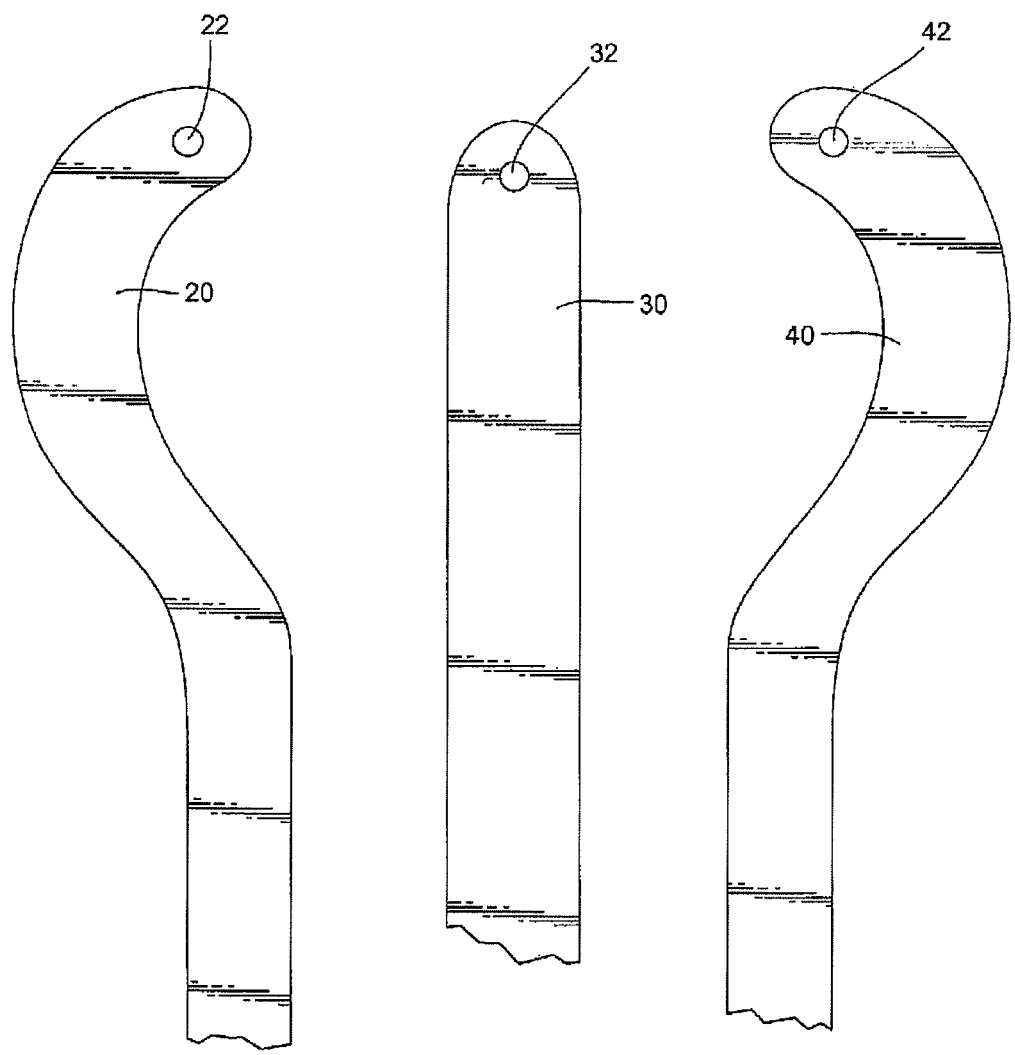
FIG. 2 is an exploded view of the leaves of the instrument of FIG. 1.
Figure 2A:
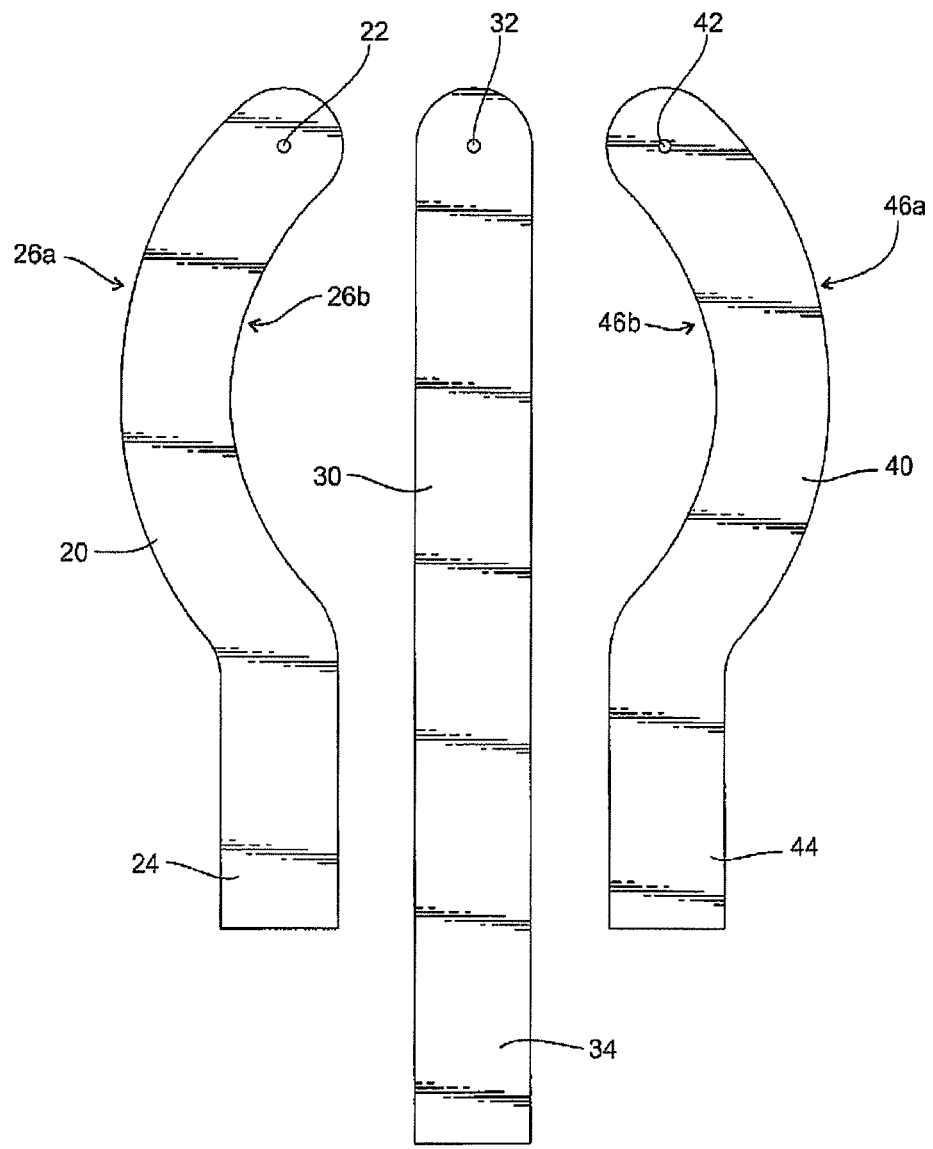
FIG. 2a is an exploded view of another embodiment of the instrument.
Figure 2B:
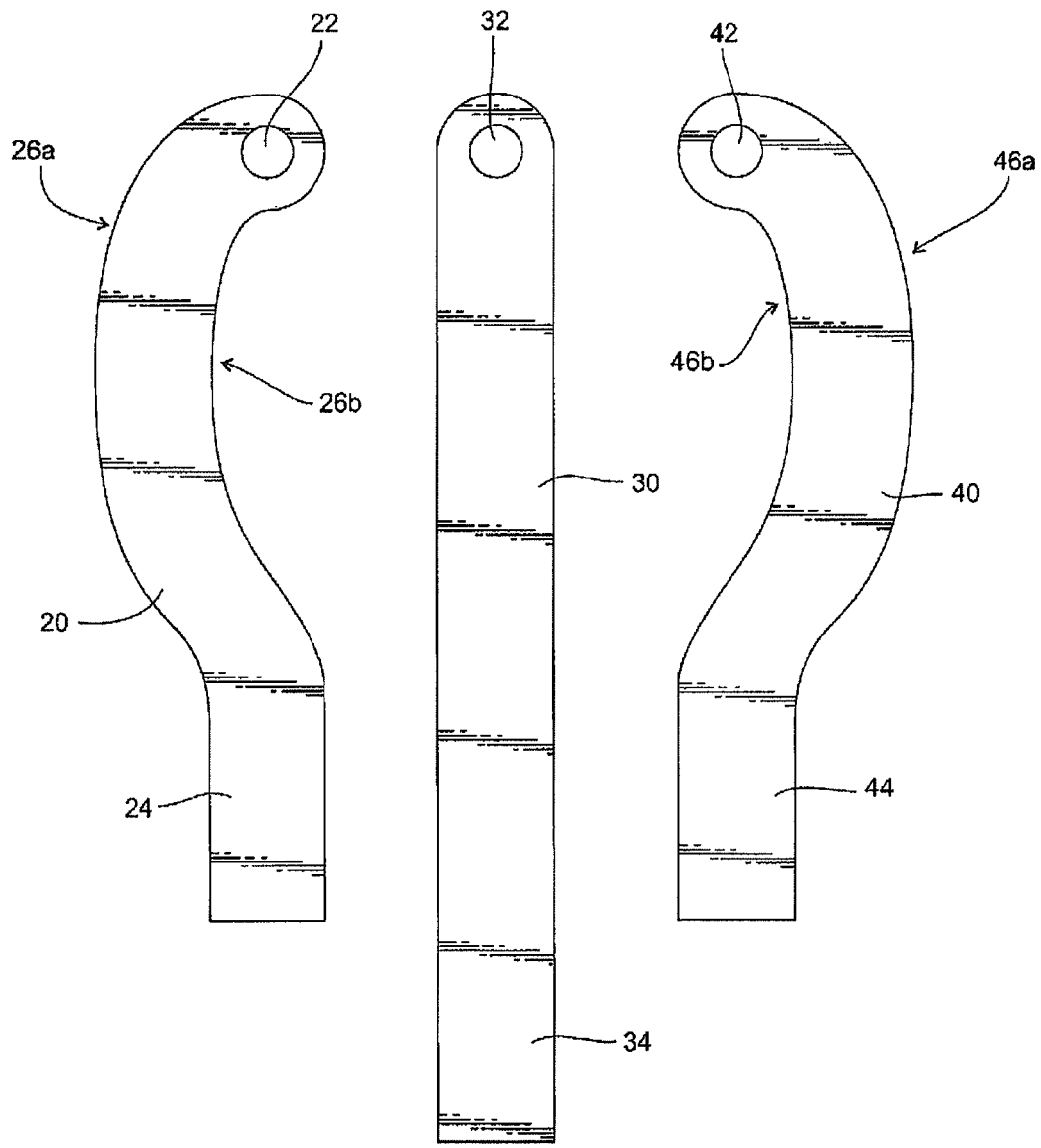
FIG. 2b is an exploded view of yet another embodiment of the instrument.

FIGS. 1-6 show an exemplary expandable shield instrument 10. As shown in FIGS. 1 and 2, this exemplary instrument includes three leaves 20, 30, 40 fixedly joined to one another, but in a manner permitting relative rotational movement of the leaves. In this embodiment, each of the leaves defines an opening 22, 32, 42 toward its respective distal end to allow for insertion of a fastener 50 capable of pivotably joining the leaves, such as a rivet, a plug, post, screw, nut and bolt, etc. At least two of the leaves, namely the outer leaves, have curvilinear outer, edges 26a, 26b, 46a, 46b, as will be further discussed below.

Each leaf 20, 30, 40 is preferably constructed of a thin, e.g. 6 mil in thickness, flat sheet material that is sterilizable and/or otherwise suitable for insertion in the eye during ocular surgery. Any suitable conventional material may be used, such as polyethylene, such as that manufactured and/or sold by Texas Technology of Austin, Tex., USA under the trademark Cleanfilm. The material should be relatively flexible to limit the likelihood of damage to ocular tissue, but should be rigid enough to permit the leaves to be somewhat self-supporting when grasped manually by their proximal ends 24, 34, 44 to permit the leaves to be manually manipulated during a procedure, and to act as a shield to prevent posterior migration of nuclear fragments, etc. In certain embodiments, the proximal end 24, 44 of each outer leaf 20, 40 includes a substantially straight-edged portion alignable with a substantially straight-edged portion of the central leaf 30 with the shield is fully expanded, such as the substantially straight-edged and aligned proximal region 24, 34, 44 of each leaf.

Figure 3:
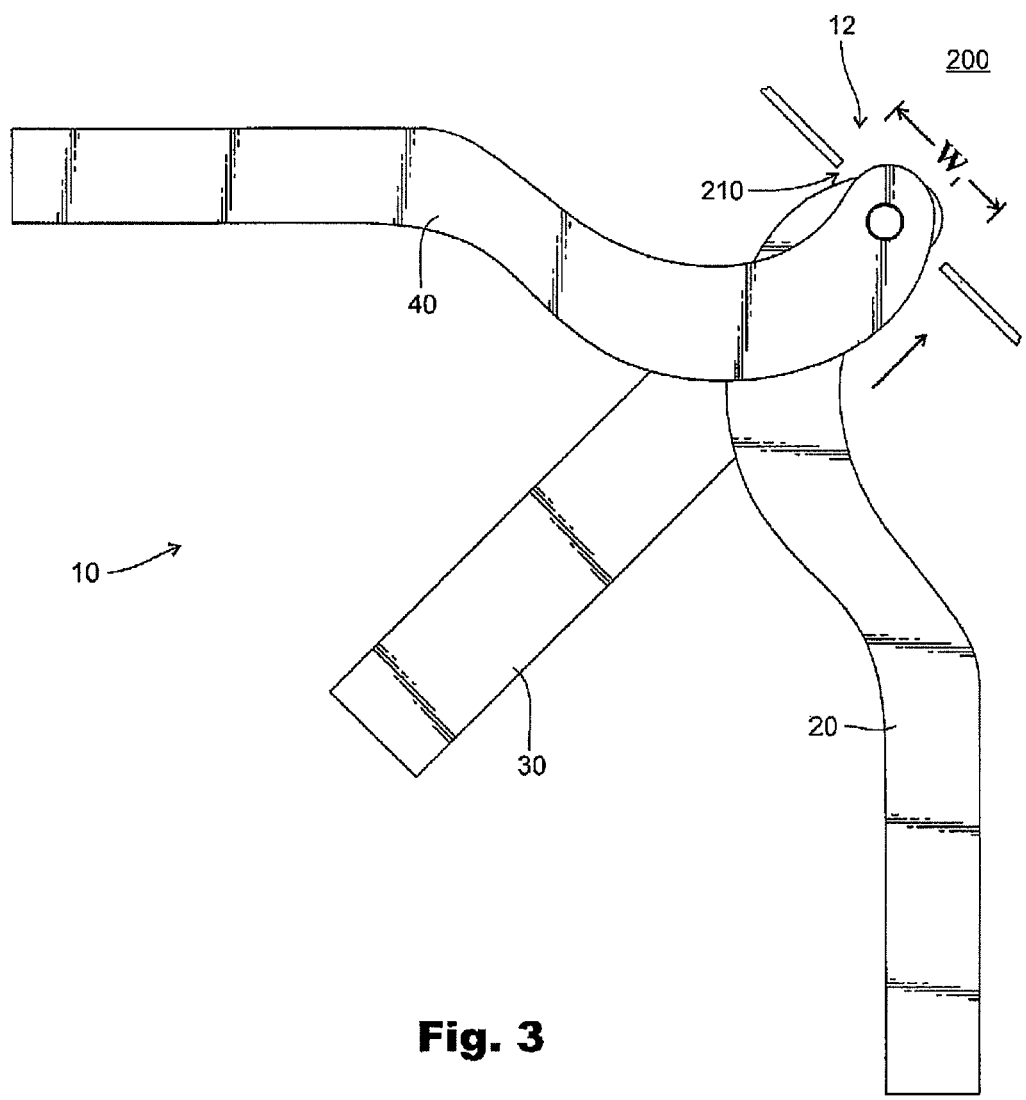
FIG. 3 is a plan view of the instrument of FIG. 1, showing the instrument in a collapsed state suitable for insertion into an incision in the eye.

FIGS. 2-6 show the instrument 10 in various states assumed during insertion of the instrument into the eye, which is shown diagrammatically as eye tissue 200 having an exemplary phacoemulsification (or other) incision 210, the eye and incision being shown in cross-section for illustrative purposes. The exemplary incision has a width $W_i$, as shown in FIGS. 3-6, of approximately 3 mm or less, as is typical of an exemplary incision made by a keratome in a phacoemulsification procedure. As best shown in FIG. 3, which shows the instrument in a collapsed state, the leading end 12 of the instrument 10 is configurable to a collapsed state in which the leading end has a width approximately equal to, and preferably less than, the width $W_i$ of the incision through which it is intended to be passed, so that the instrument may be passed into the eye with little or no damage to the ocular tissue surrounding the incision.

Figure 4:
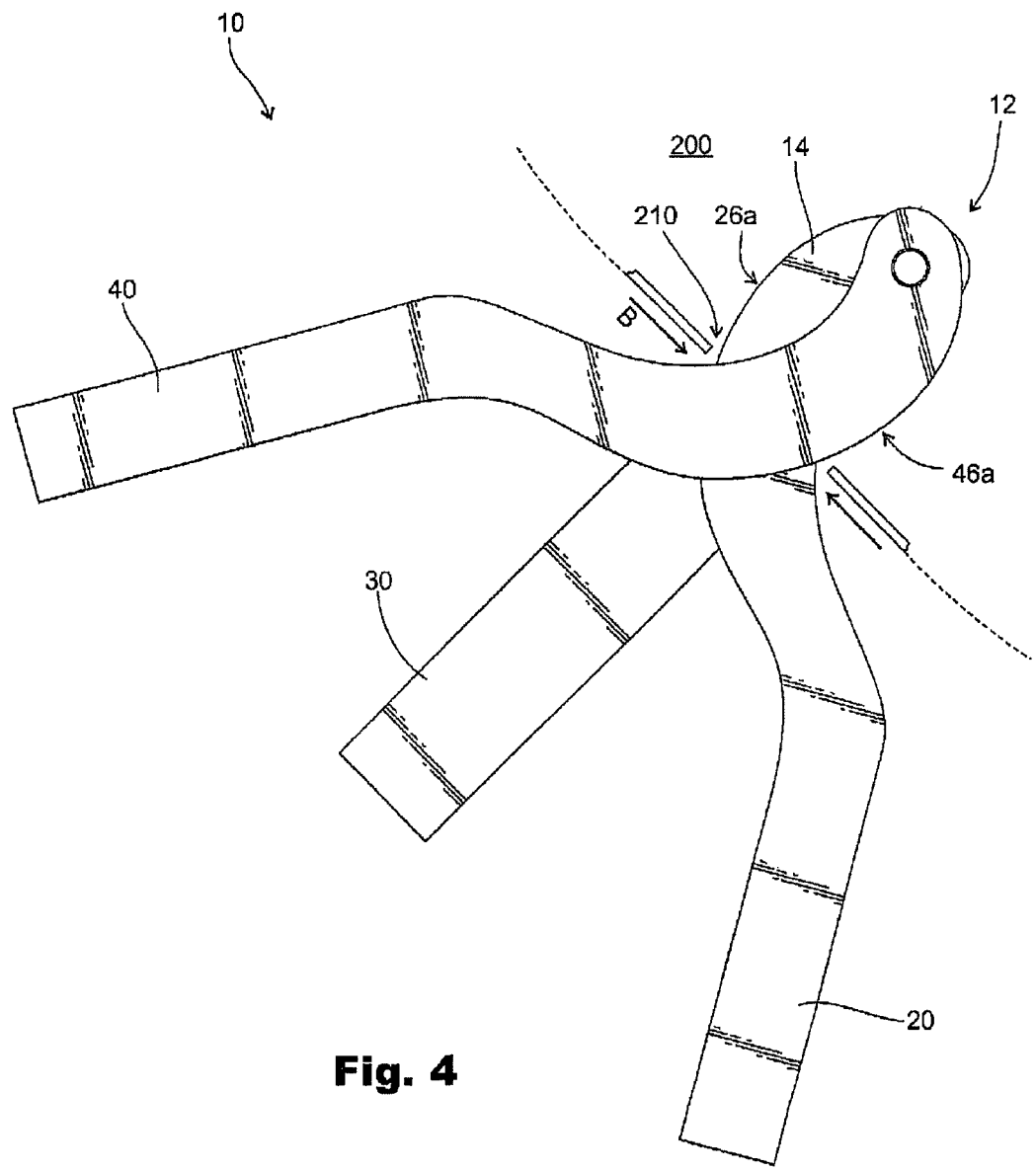
FIGS. 4 and 5 are plan views of the instrument of FIG. 1, showing the instrument in various expanded states as it is inserted through the incision in the eye.

As the instrument 10 is advanced further into the eye, as shown in FIG. 4, the outer leaves 20, 40 may be manually grasped and pivoted about the fastener 50 to expand the leaves to define a shielding portion 14 within the eye, e.g., within the anterior chamber of the eye. Additionally, the leaves may be manipulated to maintain an outer boundary B defined by the overlapping leaves, adjacent the incision in the eye tissue, at a width approximately equal to, and preferably less than, the width $W_i$ of the incision. This minimizes damage to the ocular tissue surrounding the incision resulting from passing of the instrument therethrough.

Figure 5:
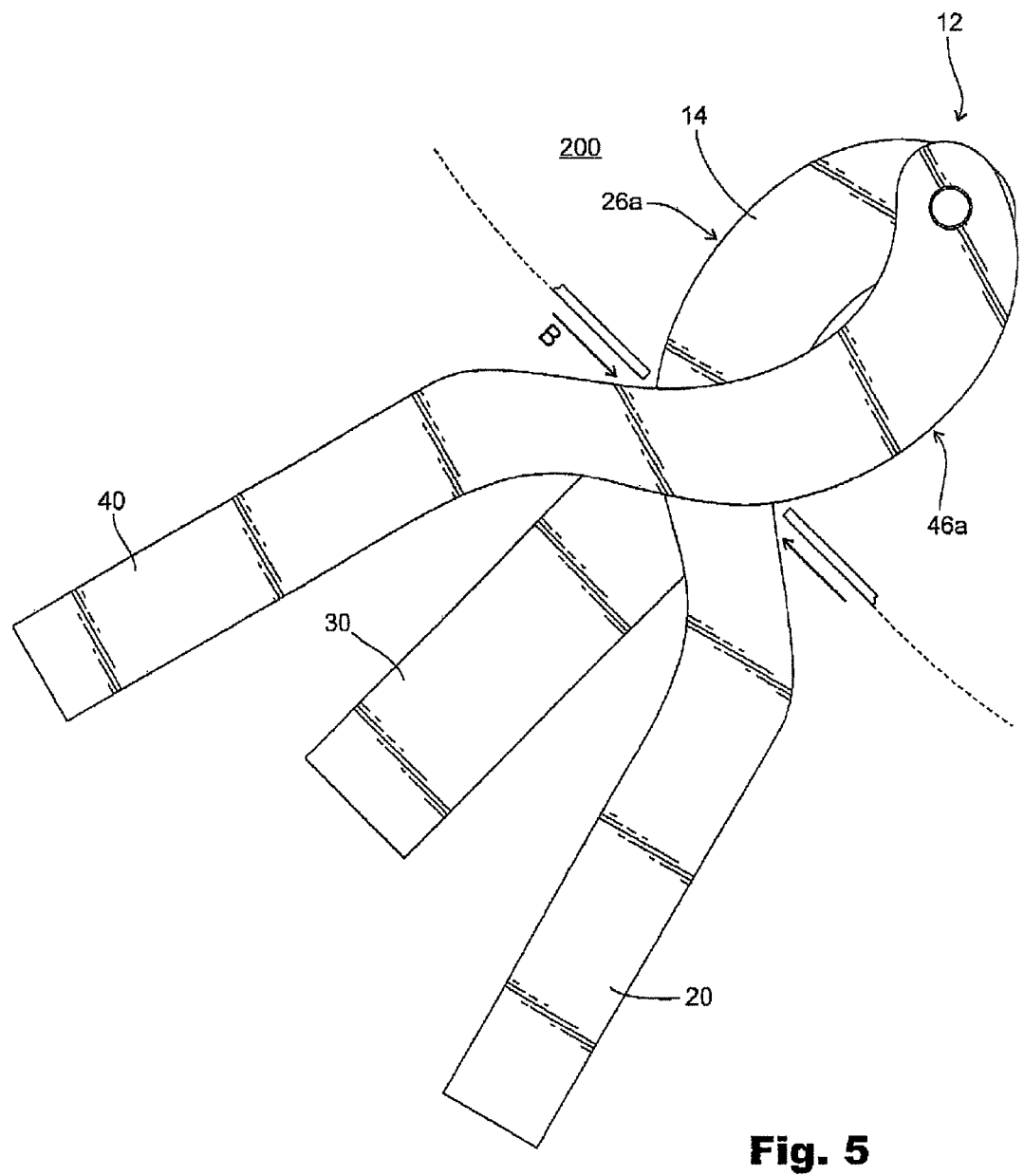

It should be noted that in this embodiment, the outer boundary B is a "sliding boundary", in that is a narrow portion that moves longitudinally relative to the longitudinal axis of the central leaf 30 from a point near the fastener 50, toward a point far from the fastener 50 as the outer leaves 20, 40 are pivoted relative to one another during insertion of the instrument into the eye. This sliding boundary permits maintenance of a minimum width of the instrument adjacent the incision 210 that approximates the incision width, and thus minimizes damage to eye tissue during insertion of the device through the incision. See FIG. 5 showing further insertion of the instrument 10 into the eye.

Figure 6:
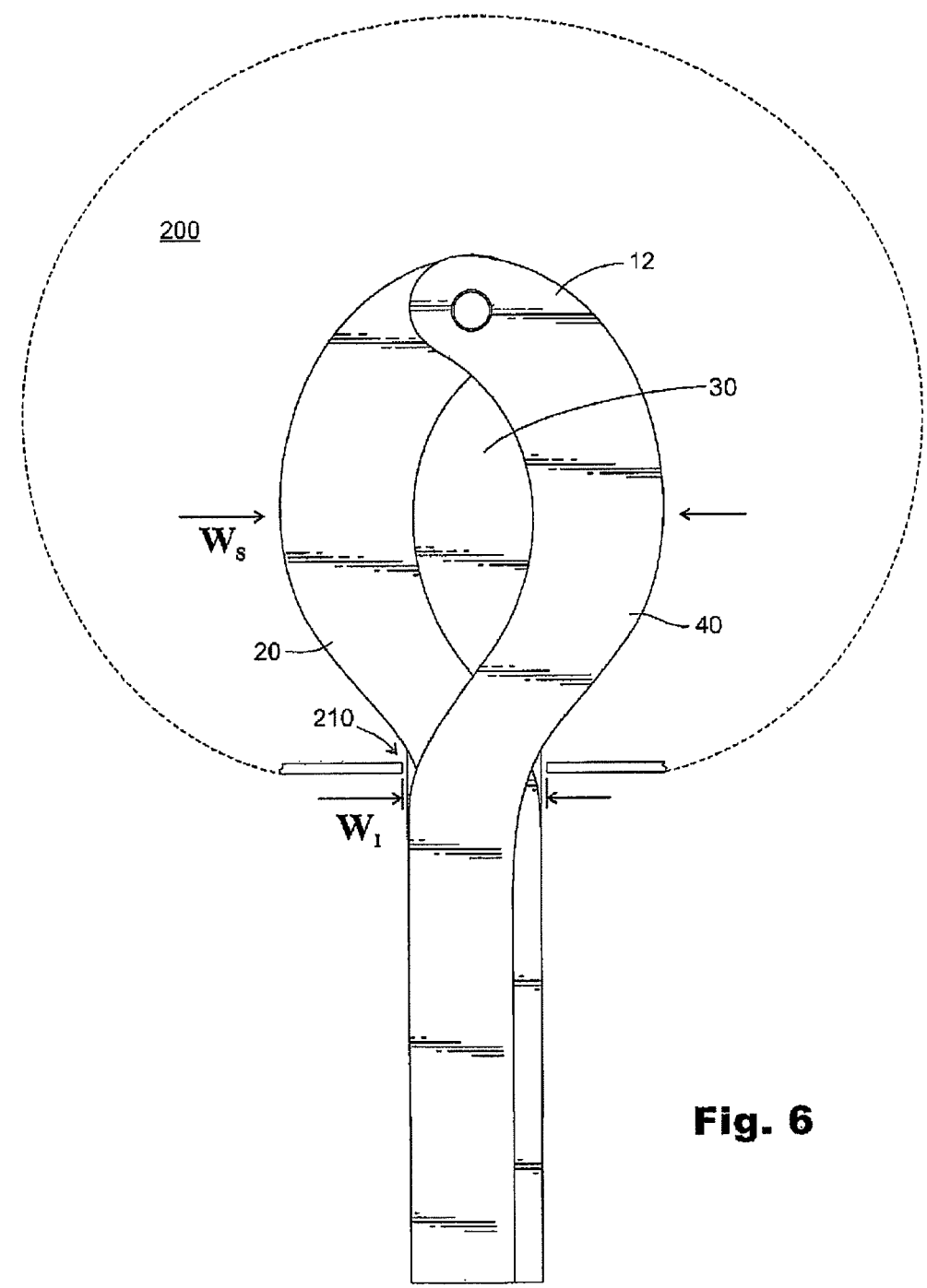
FIG. 6 is a plan view of the instrument of FIG. 1, showing the instrument in a fully expanded state in the eye.
Figure 6A:
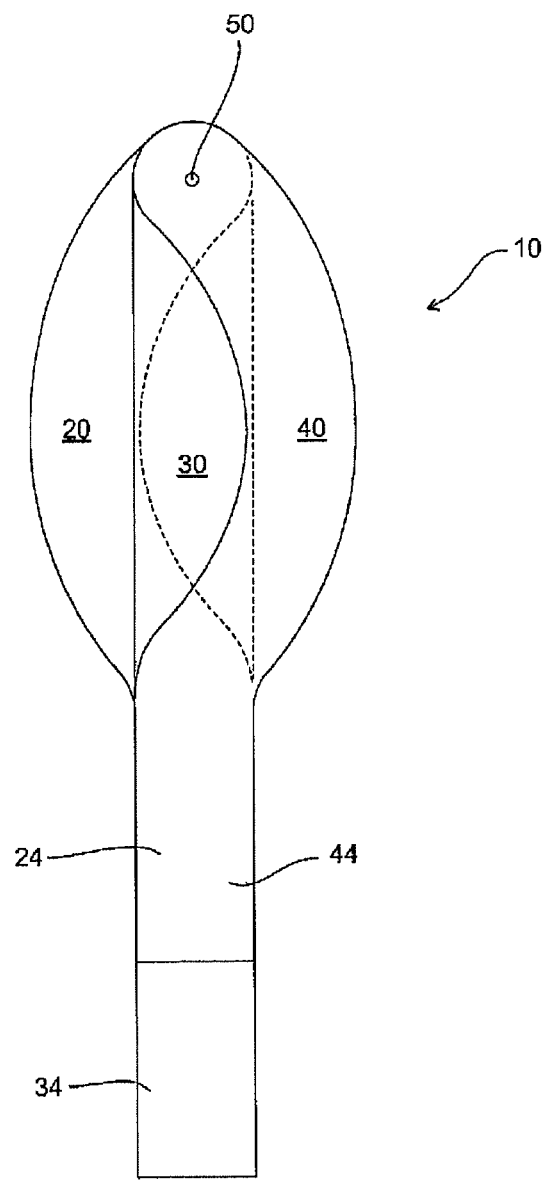
FIG. 6a is a plan view of the instrument of FIG. 2a in s fully expanded state.
Figure 6B:
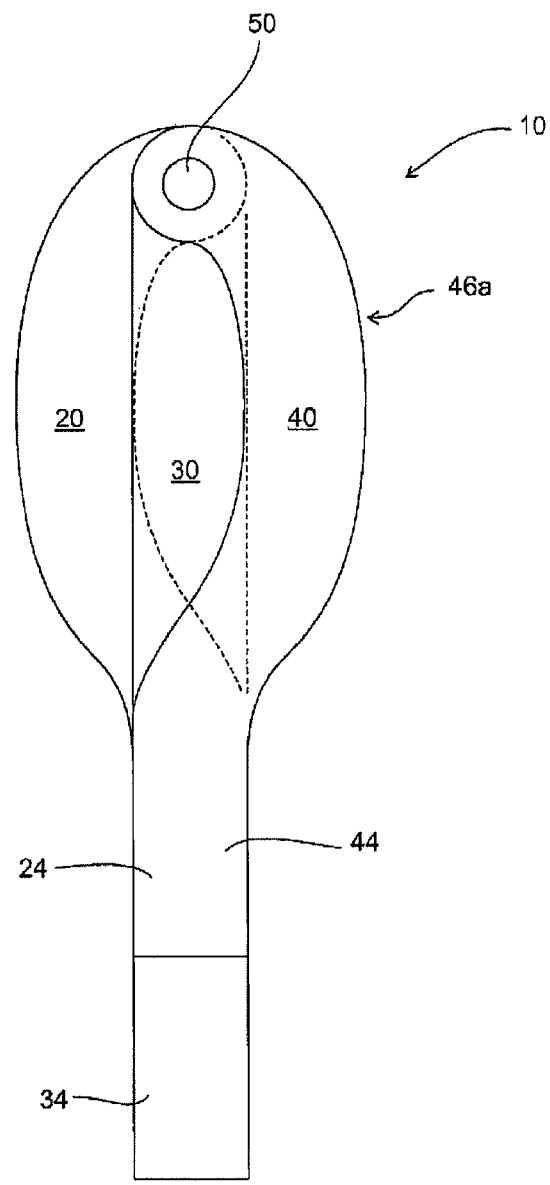
FIG. 6b is a plan view of the instrument of FIG. 2b in s fully expanded state

When the instrument is fully inserted into the eye, as shown in FIG. 6, the shield portion 12 is fully expanded to provide a maximum area of the shielding surface. It will be noted that the leaves 20, 30, 40 may overlap to provide a continuous (or substantially continuous) shielding surface area. Accordingly, it will be noted that the maximum width $W_s$ of the shield portion 12 within the eye can be manipulated to far exceed the width $W_i$ of the incision through which the instrument must be passed, as shown in FIG. 6. For example, the shielding portion 12 may have an approximate maximum length and maximum width each greater than 3 mm, and/or providing a shielding area greater than approximately 9 mm$^2$' and preferably greater than approximately 5 mm in diameter and/or greater than approximately 19 mm$^2$, and thus be suitable for occluding the posterior capsular opening, for example, which is typically about 6 mm in diameter.

It should be noted that it is possible to advance the instrument directly into the eye by manually grasping the central leaf 30 alone, and pushing the instrument through the incision and into the anterior compartment of the eye. In this insertion method, the eye tissue adjacent the incision defines a "bottleneck", and acts as a follower in a cam/follower arrangement, and causes the curvilinear (cam) surfaces of the outer leaves 20, 40 to pivot to expand the shield portion 12 as it is advanced into the eye. Similarly, the central leaf 30 alone may be grasped as the instrument is withdrawn from the eye, and the leaves will move automatically as the curvilinear surfaces 26a, 46a ride over the eye tissue adjacent the incision, to automatically move the leaves, such as into the collapsed state and in any case having the minimum width of the tool adjacent the incision to permit removal from the eye.

Figure 7:
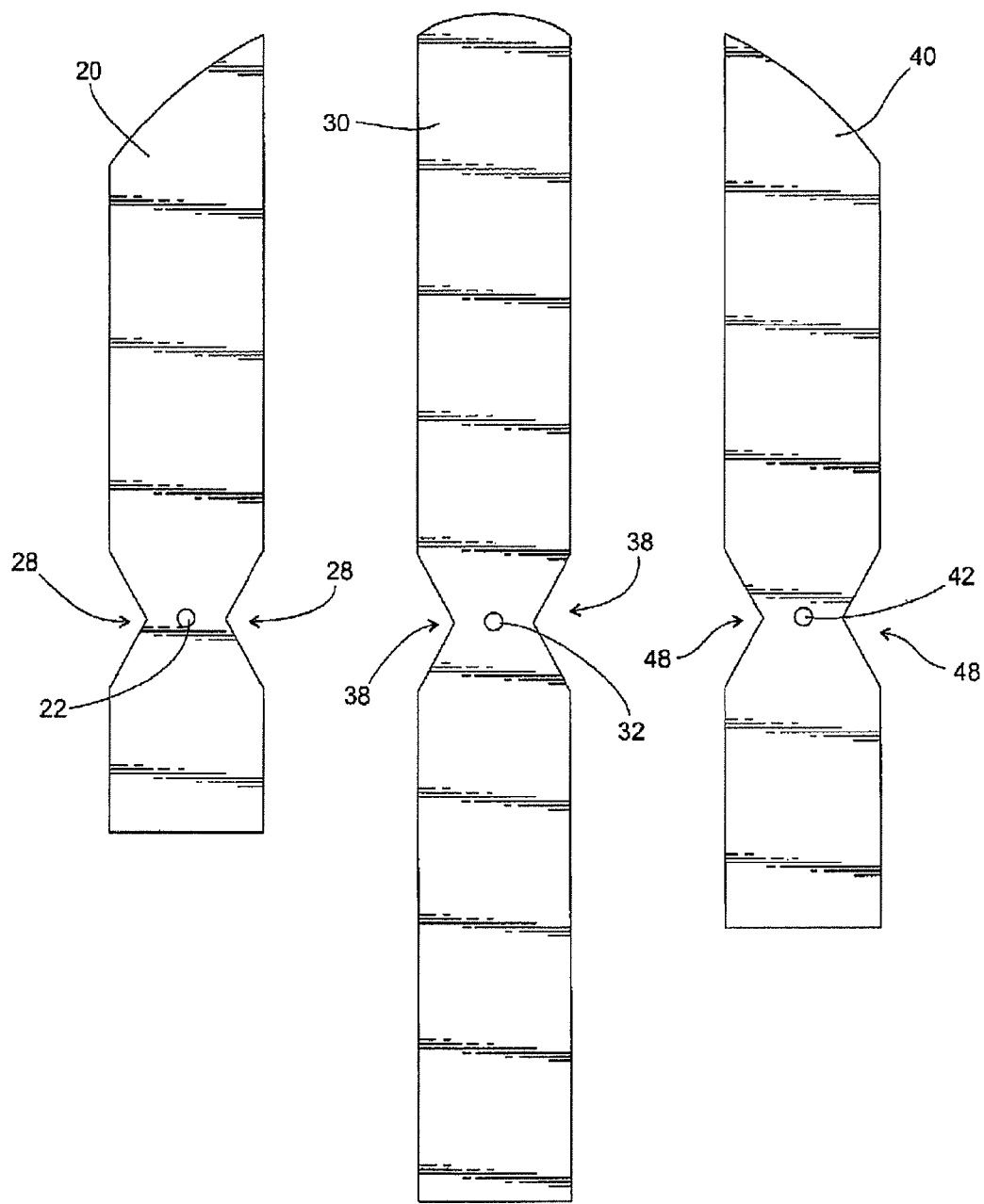
FIG. 7 is an exploded view of leaves of an expandable shield instrument in accordance with an alternative embodiment of the present invention.
Figure 8:
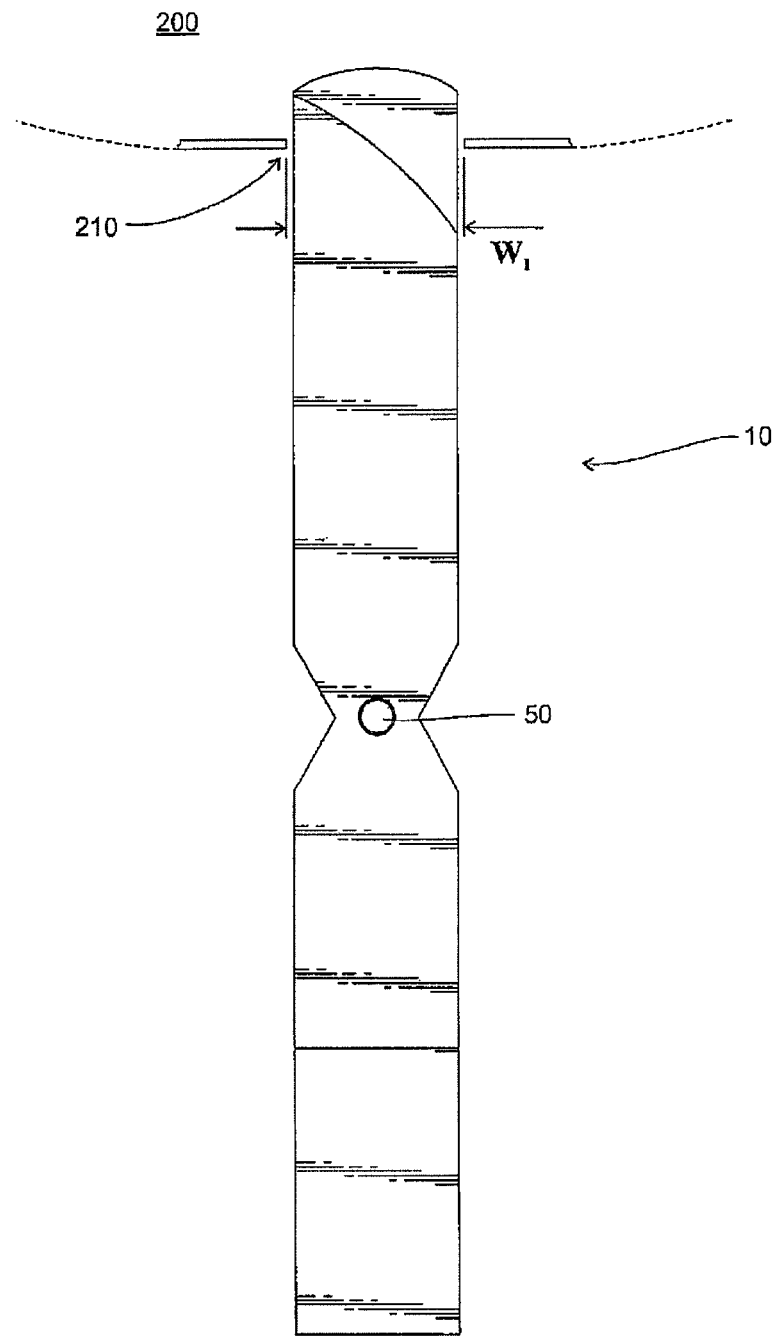
FIG. 8 is a plan view the instrument including the leaves of FIG. 7, shown in a collapsed state.
Figure 9:
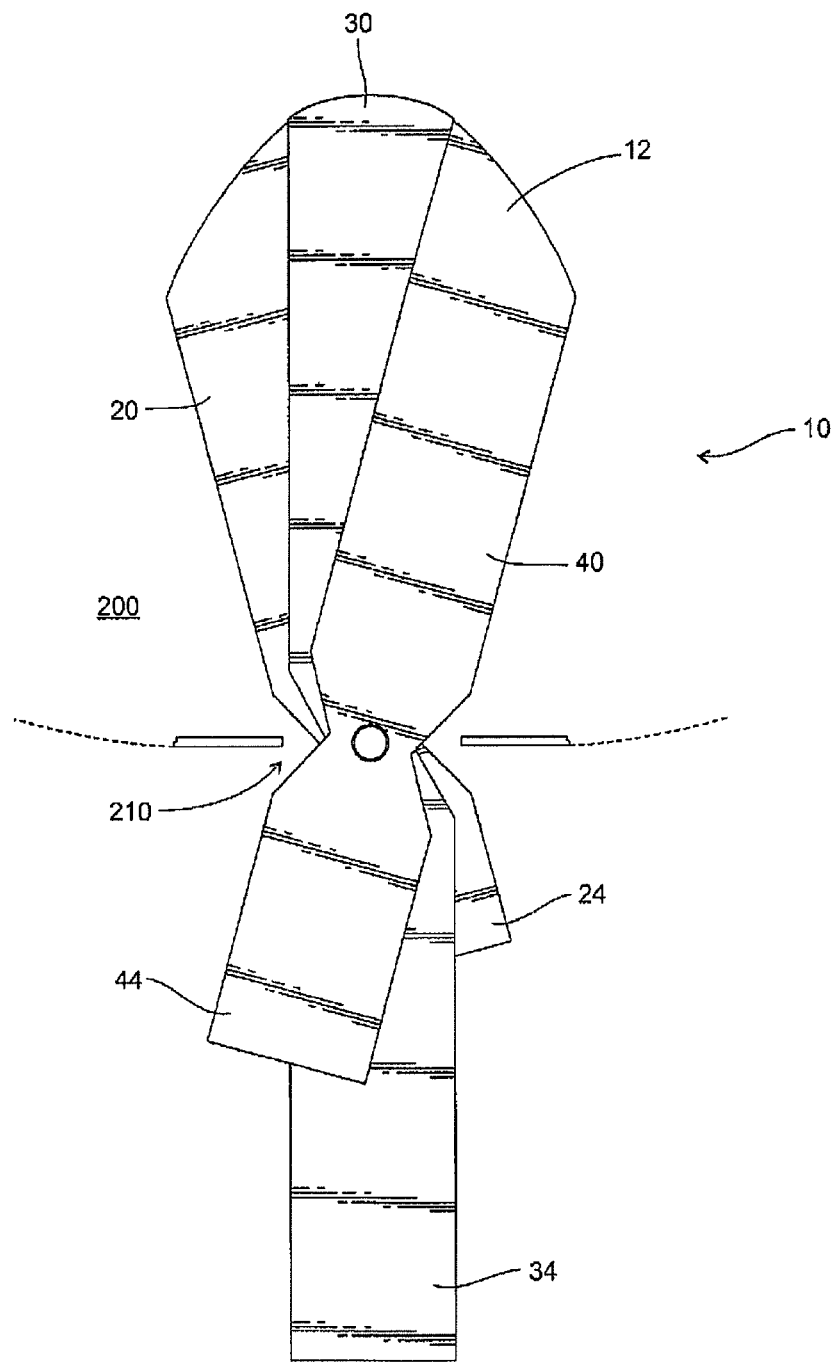
FIG. 9 is a plan view the instrument of FIG. 8, showing the instrument in a fully expanded state in the eye.

FIGS. 7-9 show an expandable shield instrument in accordance with an alternative embodiment of the present invention. The individual leaves 20, 30, 40 define openings 22, 32, 42 at which they may be interconnected or joined by a fastener 50, etc, as best shown in FIGS. 7 and 8. It should be noted that fewer or more than three leaves may be employed, as desired. In this embodiment, the leaves are generally rectangular in overall shape, and may be aligned to substantially overlap to define a collapsed state having a width less than a width $W_i$ of the incision in the eye through which it must be passed, as best shown in FIG. 8. In this embodiment, however, the outer edges of the leaves define reentrant shoulders 28, 38, 48 at which the width of each leaf is narrowed, as best shown in FIG. 7. The shoulders are positioned adjacent the fastener 50, as best shown in FIGS. 8 and 9. This permits the instrument 10 to be inserted into the eye to a point at which the shoulders 28, 38, 48 span the incision in the eye tissue, as shown in FIG. 9. The provides clearance to limit damage to ocular tissue when the distal ends of the leaves are spread apart in fan-like fashion to provide an expanded shield portion 12 within the eye 200, as best shown in FIG. 9. The distal ends of the leaves may be spread in this manner by manually manipulating the proximal ends 24, 34, 44 of the leaves 20, 30, 40, which remain outside of the eye and accessible to the eye surgeon. The leaves may be collapsed and withdrawn as desired, in a similar manner.

Figure 10:
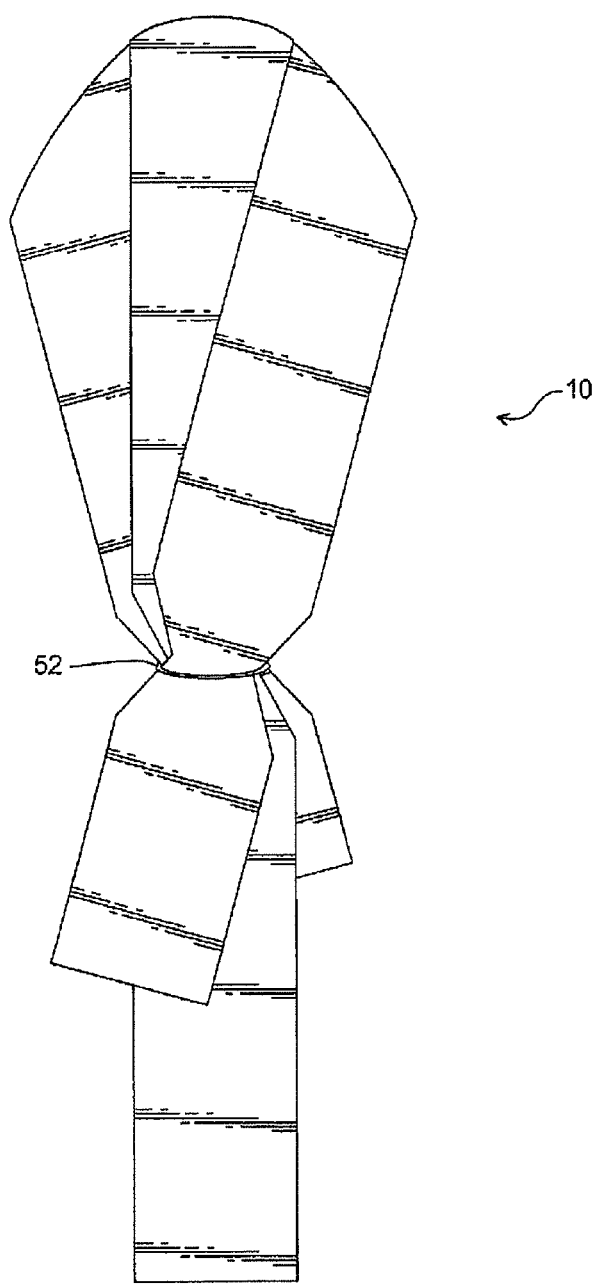
FIG. 10 is a plan view of an alternative embodiment of the instrument of FIG. 8.

FIG. 10 is a plan view of an alternative embodiment of the instrument of FIG. 8. In this embodiment, the leaves 20, 30, 40 need not include an opening for accommodating a fastener 50. Instead, an elastomeric or other constrictive band 52, may be placed around the leaves in lieu of another fastener such as a rivet to provide scissor-like pivoting action of the leaves. This device may be used, inter alia, in an eye surgery by insertion through incision in a manner similar to that described above with reference to the embodiment of FIGS. 7-9.

FIGS. 11 and 12 are plan views of another alternative embodiment of the instrument. In this embodiment, a pair of leaves 20, 30 support a relatively smooth continuous membrane 60, such as a thin sheet of polyethylene, providing a shielding area approximately 7 mm in diameter. The membrane 60 is sufficiently thin and flexible to be gathered between the leaves 20, 30, or wrapped around one or both of the leaves, to provide a collapsed state in which an outer width of the instrument is approximately equal to or less than a width $W_i$ of the incision through which it is intended to be passed, e.g. 3 mm or less. After insertion into the eye, the leaves may be separated to extend the membrane 60 therebetween to provide a shield portion 12 within the eye. For illustrative purposes, the instrument is shown in a partially collapsed state in FIG. 11, and in a partially expanded state in FIG. 12.

FIGS. 13 and 14 are plan views of yet another alternative embodiment of the instrument 10. This embodiment is similar in structure and in use to that shown in FIGS. 11 and 12. However, in this embodiment, the membrane 60 includes accordion-style pleats 62 to facilitate collapsing of the instrument. For illustrative purposes, the instrument is shown in a collapsed state in FIG. 13, and in a partially expanded state in FIG. 14.

FIG. 15 is a plan view of an alternative embodiment of the instrument of FIGS. 11 and 12. This embodiment is similar in structure and use to that shown in FIGS. 11 and 12, but further includes a fastener 50 joining the leaves 20, 30 so that they may pivot relative to one another. A rivet, as shown in FIG. 15, or similar fastener may be used for this purpose. Optionally, the leaves 20, 30 may include shoulders 28, 38 similar to those shown in FIGS. 7-10. The instrument may be positioned in collapsed and expanded states by manually manipulating the proximal ends 24, 34 of the leaves 20, 30 in a manner similar to that described above.

FIG. 16 is a plan view of an alternative embodiment of the instrument of FIGS. 13 and 14. This embodiment is similar in structure and use to that shown in FIGS. 13 and 14, but further includes a fastener joining the leaves 20, 30 so that they may pivot relative to one another. An elastic or inelastic constrictive band 52, as shown in FIG. 16, or similar fastener 50 such as a rivet, may be used for this purpose. Optionally, the leaves 20, 30 may include shoulders 28, 38 similar to those shown in FIGS. 7-10. The instrument may be positioned in collapsed and expanded states by manually manipulating the proximal ends 24, 34 of the leaves 20, 30 in a manner similar to that described above.

Although use of the instrument is described above for illustrative purposes with respect to use in a phacoemulsification procedure, it is suitable for a variety of uses. Additional exemplary uses of the instrument include, but are not limited to any invasive surgical procedure requiring a shielding or partitioning device through an incision smaller than a desired shield or partition distal end.

In posterior capsular rupture with remaining nuclear fragments, the instrument may be placed behind the fragments to prevent their posterior dislocation during the attempts at their removal;

When inserting an IOL into the ciliary sulcus in the presence of a capsular rupture, the instrument may be used to guide the lens safely over the capsular opening and into the sulcus; and If an IOL is determined to have inadequate capsular support (due, for example, to the size of a capsular tear or zonular dehiscence), the instrument may be used to guide the IOL out of the eye, providing a barrier to the posterior compartment.

While there have been described herein the principles of the invention, it is to be understood by those skilled in the art that this description is made only by way of example and not as a limitation to the scope of the invention.

The invention claimed is:

1. A surgical instrument comprising:
    a plurality of leaves, each of said plurality of leaves having respective proximal and distal end portions, the leaves being interconnected at their distal end portions by at least one fastener, the leaves being shaped to overlap to provide collectively a substantially continuous shielding surface, broader than a width of one of said plurality of leaves, intermediate said at least one fastener and said proximal end portions when said proximal end portions are manipulated into overlapping positions by a user;
    wherein the outer leaves each comprise a curvilinear outer portion, and wherein the leaves are arranged such that the instrument has a minimum width, corresponding to a width of a widest leaf, that can be selectively moved along a central longitudinal axis of the instrument between the distal end portion of the instrument and the proximal end portion of the instrument by manipulating relative positions of the proximal end portions of the outer leaves relative to the central leaf.

2. The surgical instrument of claim 1, wherein the minimum width of the instrument is less than 3 mm.

3. The surgical shielding instrument of claim 2, wherein the substantially continuous shielding surface provides a surface area that is at least double a corresponding surface area of any one leaf in the region.

4. The surgical instrument of claim 3, wherein said plurality of leaves comprises at least three leaves, including a central leaf disposed along a central longitudinal axis of the instrument, and at least two outer leaves pivotably interconnected to the central leaf.

5. The surgical instrument of claim 4, wherein each leaf is substantially flat.

6. The surgical instrument of claim 5, wherein each leaf includes a rounded distal end.

7. The surgical instrument of claim 6, wherein the outer leaves each comprise a curvilinear portion extending curvilinearly, and wherein the leaves are arranged such that the instrument has a minimum width that can be selectively moved along the central longitudinal axis of the instrument between the distal end portion of the instrument and the proximal end portion of the instrument by manipulating relative positions of the proximal end portions of the outer leaves relative to the proximal end portion of the central leaf.

8. The surgical instrument of claim 7, wherein the curvilinear portions interact with a wall of an incision when inserted therethrough to automatically adjust relative positions of the outer leaves so that the surface area of the continuous shielding surface increases as the instrument is inserted through the incision to a preselected maximum depth.

9. The surgical instrument of claim 7, wherein the the curvilinear portions interact with a wall of an incision when withdrawn therethrough to automatically adjust relative positions of the outer leaves so that the surface area of the continuous shielding surface decreases as the instrument is withdrawn from the incision.

10. The surgical instrument of claim 6, wherein the central leaf is substantially rectangular, and wherein the outer leaves comprise a generally S-curved shape.

11. The surgical instrument of claim 6, wherein the instrument has a minimum width that is located at an overlapping portion of all leaves.

12. The surgical instrument of claim 11 wherein the central leaf is longer than the outer leaves.

13. The surgical instrument of claim 1, wherein the curvilinear outer portions interact with a wall of an incision when inserted therethrough to automatically adjust relative positions of the outer leaves so that the surface area of the continuous shielding surface increases as the instrument is inserted through the incision to a preselected maximum depth.

14. The surgical instrument of claim 1, wherein the wherein the curvilinear portions interact with a wall of an incision when withdrawn therethrough to automatically adjust relative positions of the outer leaves so that the surface area of the continuous shielding surface decreases as the instrument is withdrawn from the incision.

15. A surgical instrument comprising:
a plurality of leaves, each of said plurality of leaves having respective proximal and distal end portions, said plurality of leaves comprising:
a central leaf extending linearly along a central longitudinal axis of the instrument; and
at least one outer leaf having a curvilinear portion extending curvilinearly; and
a fastener disposed at the distal end portions and interconnecting said plurality of leaves;
wherein each said at least one outer leaf comprises a curvilinear outer portion, and wherein said plurality of leaves are arranged such that the instrument has a minimum width, corresponding to a width of a widest leaf, that can be selectively moved along a central longitudinal axis of the instrument between a distal end portion of the instrument and a proximal end portion of the instrument by manipulating relative positions of the proximal ends portions of each of said at least one outer leaf relative to the central leaf.

16. The surgical instrument of claim 15, wherein a width of said central leaf and a respective width of said at least one outer leaf are both equal to a minimum width of the instrument.

* * * * *